United States Patent [19]
Cruz

[11] Patent Number: 5,653,680
[45] Date of Patent: Aug. 5, 1997

[54] ACTIVE WRIST BRACE

[76] Inventor: Mark K. Cruz, 444 Brown Trail, Hopatcong, N.J. 07843

[21] Appl. No.: 513,604

[22] Filed: Aug. 10, 1995

[51] Int. Cl.⁶ ................................................. A61F 5/00
[52] U.S. Cl. .......................... 602/21; 602/16; 482/45
[58] Field of Search .................................. 602/5, 16, 20, 602/21; 601/23, 40; 273/188 R, 189 R; 482/44–46

[56] References Cited

U.S. PATENT DOCUMENTS

| | | | |
|---|---|---|---|
| 2,767,708 | 10/1956 | Keropian | 601/40 X |
| 3,631,542 | 1/1972 | Potter | 602/21 X |
| 3,707,963 | 1/1973 | Keropian | 601/40 X |
| 4,772,012 | 9/1988 | Chesher | 601/40 X |
| 5,103,807 | 4/1992 | Makaran | 602/21 X |
| 5,170,777 | 12/1992 | Reddy et al. | 601/40 X |
| 5,364,323 | 11/1994 | Liu | 601/40 X |
| 5,380,259 | 1/1995 | Robertson et al. | 601/40 X |
| 5,466,192 | 11/1995 | Castolo et al. | 602/21 X |

*Primary Examiner*—Linda C. Dvorak

[57] ABSTRACT

The invention is a prefabricated, dynamic, interactive wrist splint/brace. The brace is simple, low profile, easily adjusted and is able to provide adjustable fixed splinting positions, active inputs, reactive force, and adjustable damping functions in all deviations. The brace will help insulate, protect and absorb vibrations and shocks the wrist joint may be subject to. The brace is simple to install, adjust, and remove by the user utilizing only their free hand. The brace is dynamic and without serious modifications can go from an adjustable static rigid splint; to a splint with limited ranges of motion; to an active or reactive rehabilitation aid; to a brace which allows universal pivoting of the wrist that does not restrict any movements yet provides safeguards to the joint to prevent re-injury. The hand piece, forearm piece and strapping are dimensioned to be able to provide support and varying pressure to the transverse metacarpal ligaments, the carpal ligaments, the intercarpal ligaments and to the transcarpel ligaments.

11 Claims, 7 Drawing Sheets

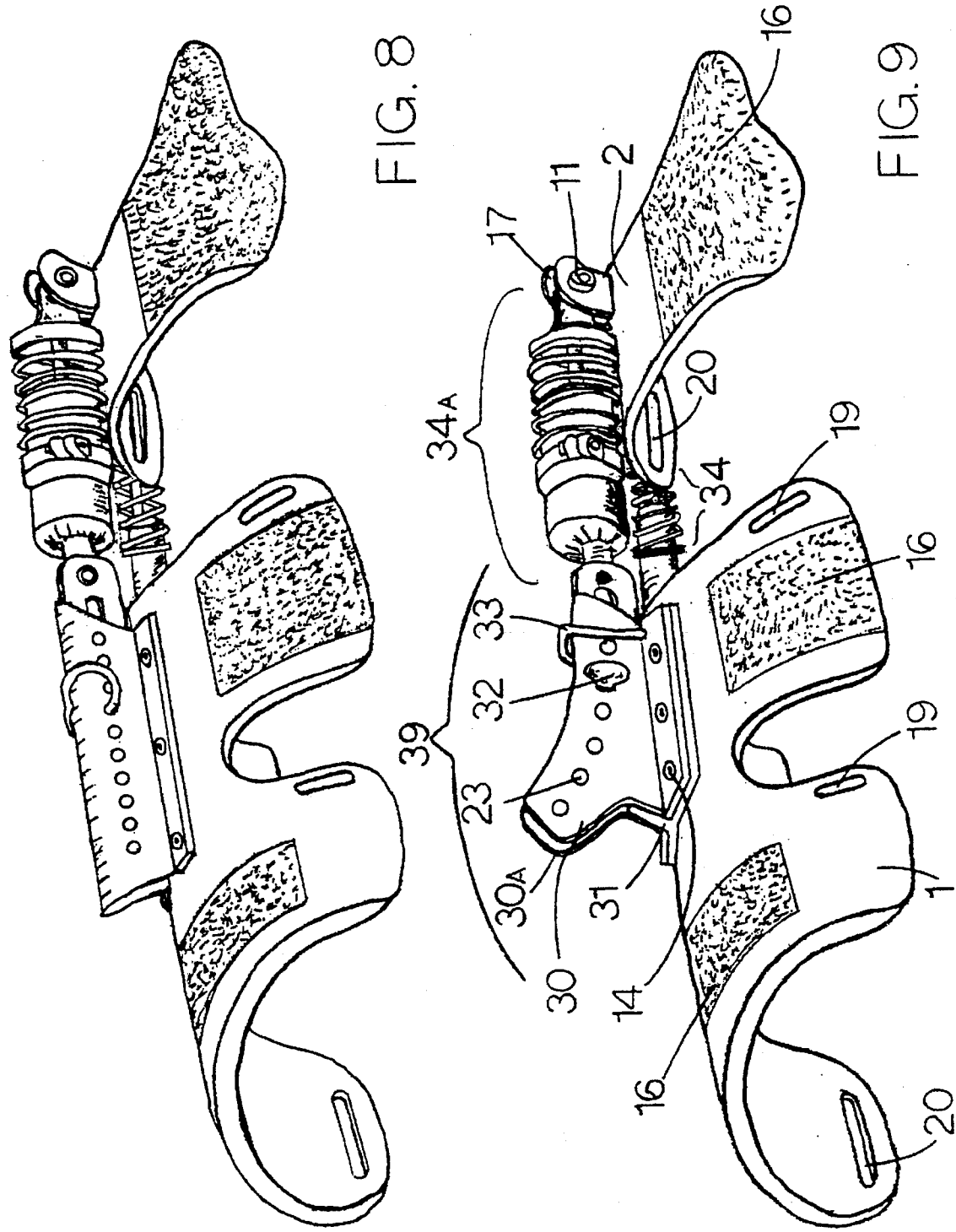

ACTIVE WRIST BRACE

BACKGROUND OF THE INVENTION

1. Field of the Invention:

The invention relates to an active wrist splint or a wrist brace, more particularly a wrist brace which is fitted to the forearm and hand. The brace is to be used in the rehabilitation of the wrist joint through rigid splinting, through application of resistance and force; to be used to lessen shock and vibration to the joint; to be used to apply specific pressure and support to the ligaments of the wrist and hand and to be used as a tool to help prevent injury or re-injury to the wrist by interactively damping shocks to the joint and by helping to prevent the wrist from exceeding its preset ranges of motion in all deviations.

Current art may satisfy one or more of the criteria throughout complex means but no brace satisfies all the criteria in a simple user friendly manner. No art form provides for shock and vibration absorption in all deviations through adjustable dampers. No art form provides interactive damping, force application, resistance, and adjustable ranges of motion/lock out to the wrist joint while at the same time providing support to specific ligaments of the wrist and hand.

2. Description of Related Art:

Current art forms offer different means to restrain the wrist in a variety of fixed positions during the healing process. Some art forms claim to be dynamic in the sense that the fixed positions are adjustable in one or two deviations. Some art forms provide force through means of springs, coils, elastics, tension beams, and screws to promote or resist hand movement up or down. None provide for interactive easily adjustable dynamic control of flexion, extension, ulnar, and radial deviations. Some may be adjusted to fixed positions in all deviations but none allow the interactive controlled application of the rate of movement, force application, resistance, damping, and range limitation in all deviations. Most art forms require significant modifications to achieve multiple functions and none provide for adjustable damping.

Reese Sr., U.S. Pat No. 5,279,545 claims to provide a simple brace to support and limit the movement of the wrist, one that is easily worn and adjusted. He accomplishes this but unfortunately his brace only provides adjustable limits of motion to the wrist. Reese Sr. defines the short comings of other related art: "Corbett, U.S. Pat. No. 2,312,523 discloses an adjustable tension splint which includes a front hand grip which limits the use of the users hand and requires loosening and tightening of a plurality of screws in order to adjust the tension of the splint. Similarly, the derotation brace of Carter, U.S. Pat. No. 5,002,044 utilizes a number of pins to limit the range of motion of parallel hinges on the brace. It would be substantially difficult for a user to adjust the brace to a more desirable position during use, and use of the hands would be limited". Furthermore, the brace largely limits the movement of the wrist joint to flexion or extension and has minimal provision for ulnar/radial deflection and no practical provision to apply positive force in either ulnar or radial deviations.

"An adjustable wrist splint such as Lindeman, U.S. Pat. No. 4,677,971 which enables lateral movement of the wrist is limited with regard to the disposition of the hand relative to the forearm". The brace is further limited in that it can only provide resistive forces, no positive forces. It cannot apply resistive forces in all deviations interactively. It takes a serious modification of the brace to accomplish isolated resistance. The brace could not be utilized in a large variety of circumstances much like the universal articulated splint of "Deprospero, U.S. Pat. No. 4,719,906 which includes an elaborate hand splint wherein each finger on the hand is immobilized such that an individual cannot use their hand if necessary".

Carter, U.S. Pat. No. 5,254,078 discloses a complex splint designed to provide a static but adjustable degree of up and down pressure to the hand while allowing lateral movement of the wrist. It accomplishes this through a "detailed process of manipulating a plurality of stop members". Pressure is applied to promote either a volar or dorsal transrelocation of the distal carpel row and to allow the wrist to pivot about a single axis which is ideal except limiting in application many of the same ways as Marx, U.S. Pat. No. 4,790,300 is Marx's brace applies positive force to make the wrist move up or down but also pivots in only one axis and requires a serious modification of the bulky rigging to accomplish this.

SUMMARY OF THE INVENTION

The present invention, a prefabricated, dynamic, interactive wrist splint/brace, is a simple, low profile, easily adjustable brace which has the capacity to provide active inputs, reactive forces, and damping functions in all deviations. The brace allows for static splinting and for adjustable ranges of motion/lock out in all deviations. The brace is able to apply pressure and support to the many ligaments of the hand and wrist. The brace is simple to install, adjust, and remove by the user utilizing only their free hand. The brace is dynamic and without serious modifications can go from a static rigid splint; to a splint with limited ranges of motion; to an active or reactive rehabilitation aid; to a brace which allows universal pivoting of the wrist that does not restrict any movements, yet provides safeguards to the joint to prevent re-injury.

The invention consists of a hand piece and a forearm piece linked together through the unique mounting and application of spring loaded dampers. These two pieces are made from aircraft grade aluminum sheet or of thermoplastic material and dimensioned to fit the dorsal surface of the hand and forearm respectively. Both materials are easily malleable and strong. These pieces are lined on the contact surface with a self adhesive closed cell foam. These pieces are dorsally fastened to the hand and forearm through typical hook and loop fasteners such as Velcro.

Mounted on the top of the forearm piece is the slip link, this link provides a unique mounting means for the top spring loaded damper. The link is a thin composite rectangular shaped piece typically made from carbon fiber composite. The link has a hole at either end and a centered slot running from front to rear of the link.

The link is kept in close tolerance on four sides to the forearm piece in an aluminum housing. The housing has mounting flanges at its base and horozontal holes drilled through the side running from end to end of the link. The holes are designed to line up with the slot in the link. The housing is mounted to the forearm piece through rivets or like fasteners. The link is slideable inside the housing. The link's fourth side, or the side not encased by the shroud runs directly on the forearm piece or on a saddle which is mounted/sandwiched between the forearm piece and the aluminum housing surrounding the link. The link slides upon this means. A shear pin; or roller; or bushing; or bearing is inserted through the front portion of the aluminum shroud and through the slot in the link. The link rides upon this means. Small holes are spaced approximately 0.062 inch apart, parallel with the long side of the link and centered to line up with the slot in the link which runs inside the housing. The holes run from the front to rear of the housing. The holes are for a shear clip, pin or thumb screw intended to lock or limit the range of travel of the slip link.

Mounted at the front of the link is a spring loaded damper. The damper mounts at one end to the front of the link and at the other end to the dorsal surface of the hand piece. The spring loaded damper is mounted at either end through a spherical bearing and tapered compression spacers. The rear surface of the slip link and the front spring loaded damper mount are curved to accept hooking of elastics. The spring on the damper is easily changeable and also adjustable in place through a moveable locking collar. The spring loaded damper may also be fitted with varying length clips which lock it fully extended or provide for limited ranges of compression for the damper. The dampers are internally and externally adjustable to provide a full range of damping from soft to stiff.

The forearm piece and hand piece are also connected on the ulnar side of the brace with a laterally mounted spring loaded damper. This damper is similar to the top mounted damper and is mounted to the forearm piece and hand piece through spherical bearings and tapered compression spacers. Both mounts for the damper are also designed for the hooking of elastics between them.

An object of this invention is to stabilize the wrist joint and provide the wrist with support.

One other object of this invention is to provide an adjustable free play zone of movement for the wrist.

Another object of this invention is to provide fully interactive adjustable ranges of motion/lock out from rigid to a normal unrestricted range of motion for the wrist.

Yet another object of this invention is to be able to provide easily adjusted varying degrees of resistance to movement of the wrist in all deviations.

A further object of this invention is to be able to provide easily adjusted varying degrees of force to the wrist in all deviations.

Another object of this invention is to absorb and dampen vibrations the wrist joint may be subject to.

Yet another object of this invention is to absorb and dampen shocks which the wrist joint may be subject to.

A still further object of the invention is to provide a brace for the wrist, which due to the adjustable dampers, their mounting, and the unique slideable lockable link, affords the wearer control over movement ranges, movement rates, and inputs throughout the wrists natural range of motion and does not restrict the wrists movement to single planes or axis that only permit unnatural mechanized movements.

One more object of the wrist brace is to be able to provide a rotational force in measured inputs to the wrist joint, specifically applying a rotational force around the capitate bone of the wrist while applying pressure to the second and third metacarpal bones promoting a volar or dorsal transrelocation of the distal carpal row.

Yet another object of the invention is to be able to provide a rotational force to the wrist joint without adding compressive forces to the joint.

Still another object of the invention is to be able to provide support and varying degrees of compressive force to the transverse metacarpal ligaments, the carpal ligaments, the intercarpal ligaments and to the transcarpel ligaments.

One final object of the invention is to be able to provide many of the stated functions interactively easily and without any serious modifications to the brace.

Additional advantages, objects and novelties of this invention will become apparent in the following detailed description.

BRIEF DESCRIPTION OF THE DRAWINGS

All drawings refer to a brace designed for the left hand. Braces for the right hand would be the exact opposite of the versions depicted.

FIG. 8 is a radial three quarter view showing the preferred embodiment of the brace less mounting straps.

FIG. 9 shows a radial three quarter view of the brace with a compression link installed in place of the preferred slip link.

DETAILED DESCRIPTION OF THE INVENTION

Figure 1:
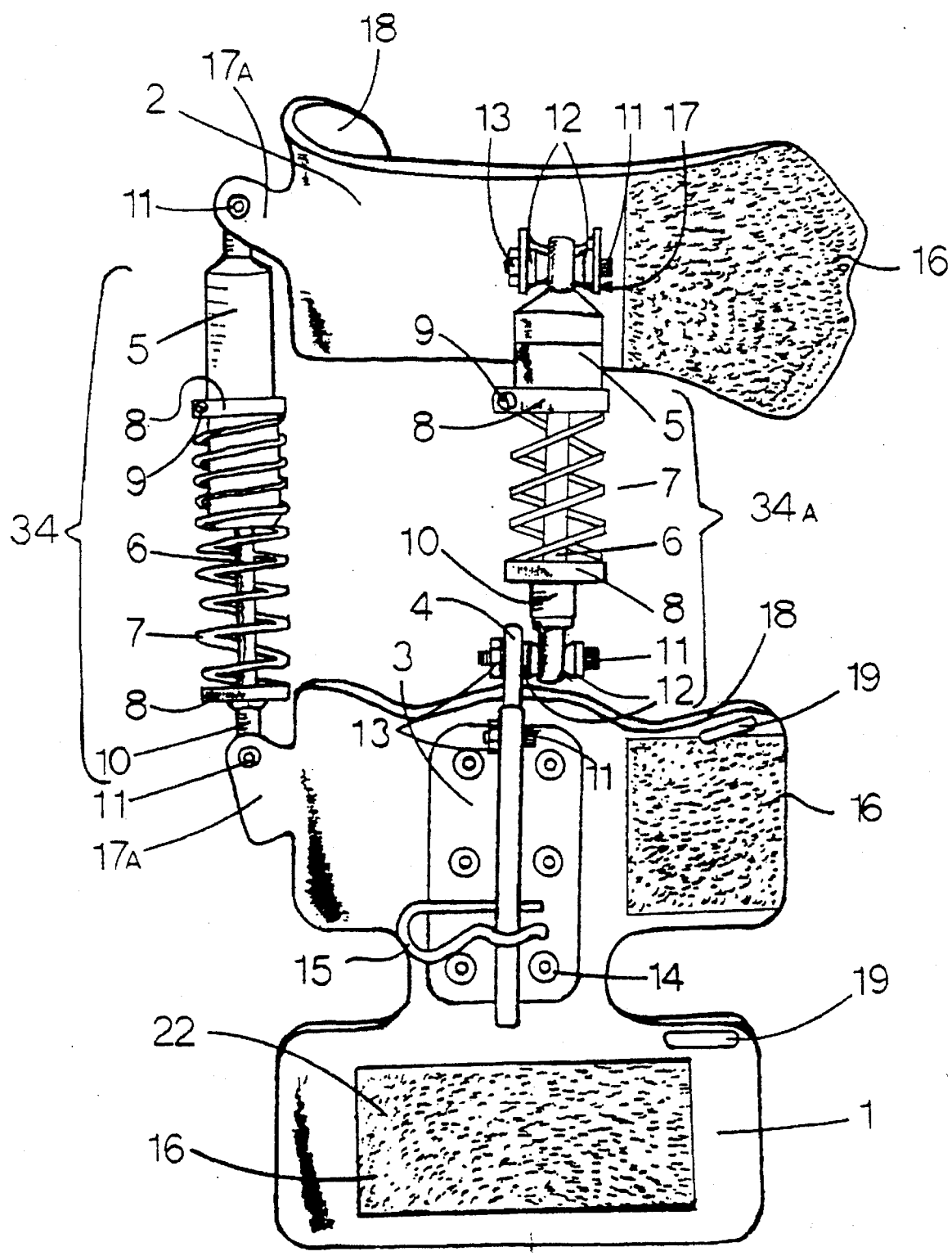
FIG. 1 shows a top view of the preferred embodiment shown for the left wrist.
Figure 2:
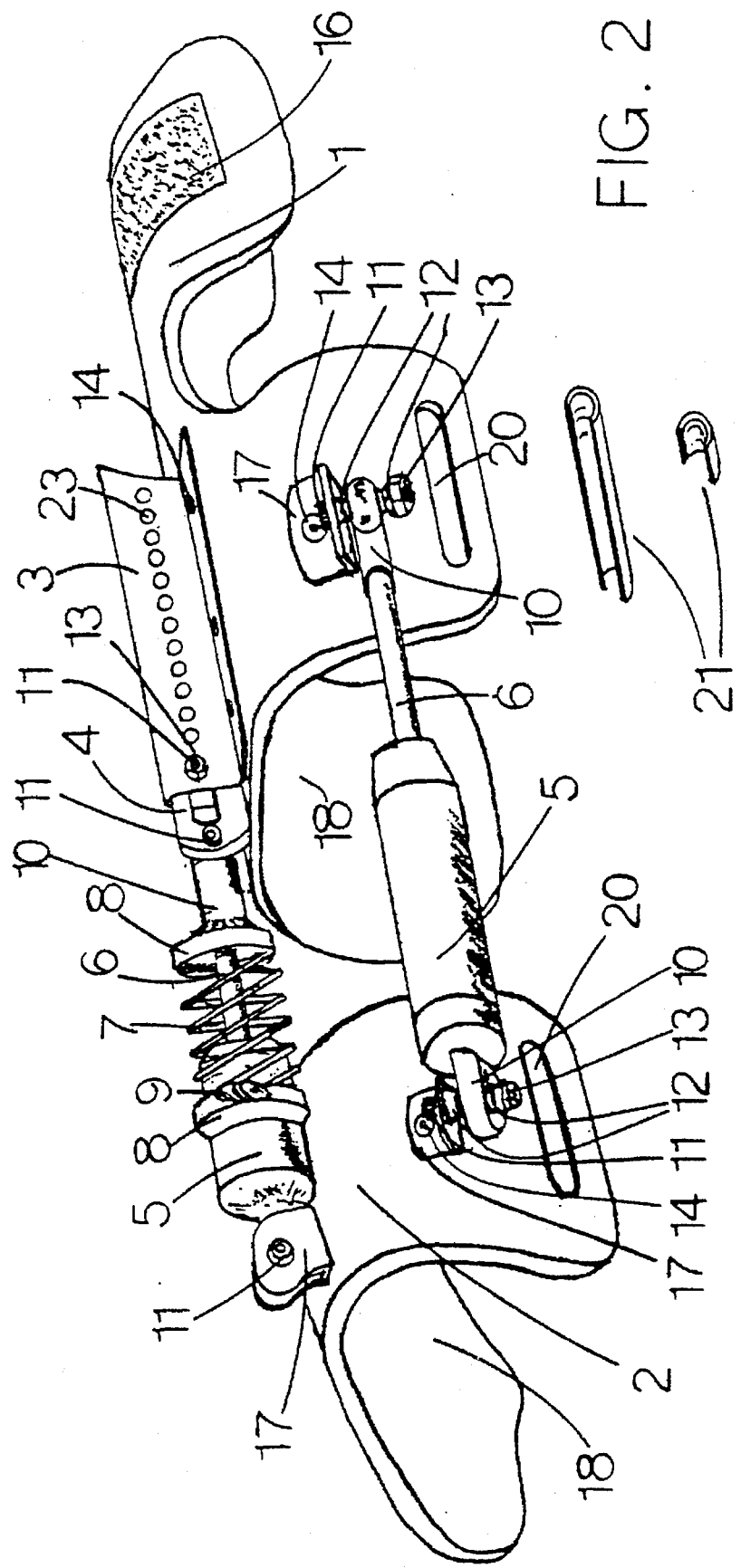
FIG. 2 illustrates an ulnar side view of the brace as seen in FIG. 1 less the spring on the outer damper. This view shows the lock out clips which fit the damper shaft.

FIG. 1 through FIG. 8 disclose in detail the preferred embodiment of the invention. FIG. 1 shows a top view of the forearm piece 1 and the hand piece 2. Both pieces are formed from either aircraft grade 0.031 inch aluminum sheet or from 0.125 inch thermoplastic sheet of the latest technology. Both pieces are lined on the contact surface with closed cell adhesive back foam padding 18. The forearm piece has oval slots cut in several positions. The two slots 20 in FIG. 2 are designed to receive D ring loop straps 35, FIG. 7 such as Velcro fasteners which are used to secure the forearm and hand pieces to the wearer. The D ring straps are easily removable from the brace for cleaning or substitution with varying degrees of stretch strapping. Strips of adhesive back hook strip 16 are applied to the forearm piece and the hand piece as shown in FIG. 1, and receive the loop straps. The rear forearm mounting strap is not of D ring style and is simply a loop strip which fastens on both sides to the adhesive back 16 hook strip at location 22. The two other slots 19 FIG. 1 are used as in FIG. 4 to mount elastics 28 from the rear position 19 to the foreword shock mount position 17. These elastics will help apply positive forces to promote radial deflection in the wrist.

Figure 4:
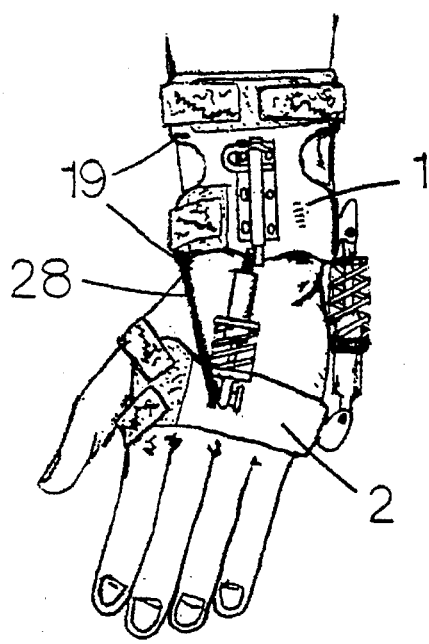
FIG. 4 shows the preferred embodiment mounted on the wrist with an elastic installed promoting radial deflection in the wrist joint.
Figure 5:
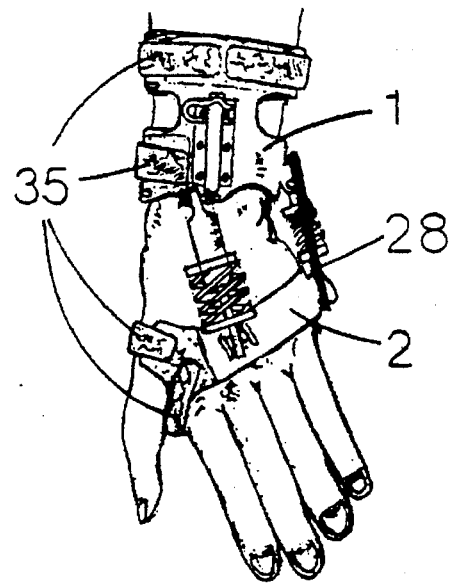
FIG. 5 shows the brace mounted on the wrist with an elastic installed to promote ulnar deflection in the wrist.
Figure 6:
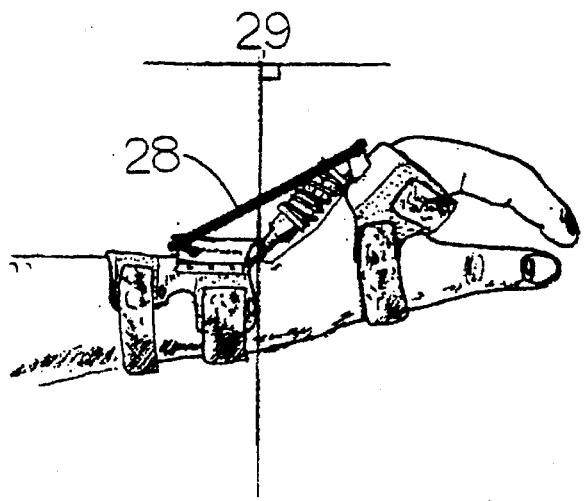
FIG. 6 shows the brace mounted on the wrist with an elastic installed to promote flexion in the wrist.

FIG. 2 illustrates an ulnar side view of the brace with the spring removed from the side damper. It also shows mounting tabs for the side damper 17, which are fabricated from thin 0.031 aluminum and are riveted 14 to the forearm piece 1 and the hand piece 2. Tabs may also be formed from the hand piece and forearm pieces, 17a FIG. 1 respectively, and bent into position. Mounting tabs can be different shapes and sizes but generally must be curved as shown in FIG. 1, tab 17a to accept the hooking of elastics as shown in FIGS. 4, 5, 6, character 28.

Figure 3:
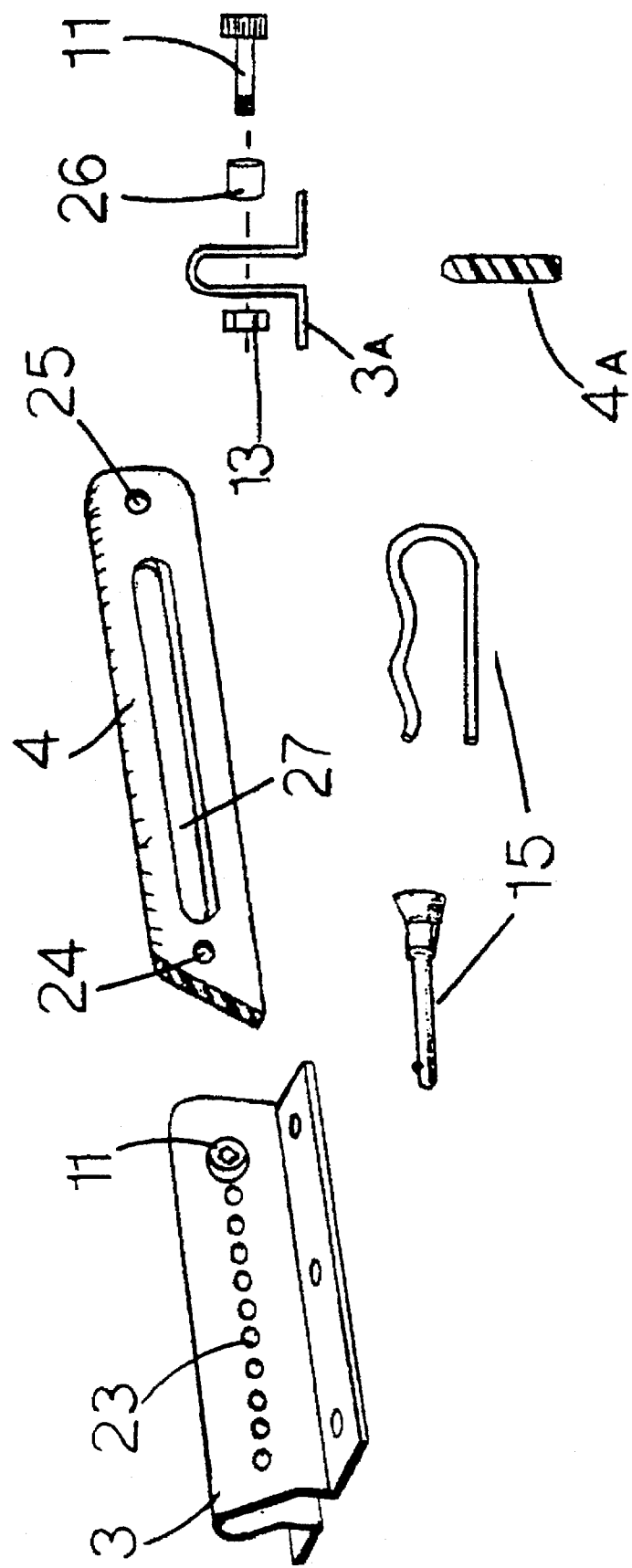
FIG. 3 is an enlarged view of the preferred slip link and its components.

FIG. 3 illustrates an enlarged expanded view of the preferred embodiment of the slip link assembly which is mounted on top of the forearm piece 1. The link housing 3 is mounted centered on the top and butted to the front of the forearm piece 1. The slip link assembly consists of an aluminum housing 3 which is designed to surround the slip link 4 in close tolerance and which has mounting flanges to be riveted to the forearm piece. The housing has holes drilled in line, spaced 0.062 apart which receive the slip link locking clip or shear pin 15. The slip link 4 is a thin rectangular approximate 2.75 inch by 0.625 inch by 0.125 inch composite of either carbon fiber, polyester or nylon. The link has a hole 25 at the front end for the mounting of a spring loaded damper 34. There is another hole at the opposite end 24 which when lined up with one of the many holes 23 in the slip link shroud 3 a pin 15 is inserted to lock the link in place. The link has a slot 27 running between the two holes 24 & 25 in the link. When pin 15 is inserted in one of the shroud holes 23 and through the slot 27 in the slip link, the links range of travel may be limited to a variety of lengths providing an adjustable free play zone of movement. The link 4 is held in the slip link housing with a bushing 26 that rides on a mounting screw 11 which is secured by a nut 13. The bushing 26 rides inside of the slip link slot 27 and on a mounting screw 11.

Ideally, two adjustable spring loaded dampers 34 & 34A FIG. 1 are mounted between the hand piece and forearm piece. Both mounting ends axis of the top and side damper are perpendicularly opposed. The top damper 34a mounts to the front hole in the slip link 25 at one end and to the hand piece at the other end at the damper mounting tab 17. This tab 17 is also curved to accept the hooking of elastics. This damper mounting tab 17 is located on the hand piece generally between the second and third metacarpal bones of the users hand.

The side damper 34 FIG. 1 is mounted at both ends to mounting tabs 17 or 17a. The damper assembly 34 FIG. 1 is mounted on the ulnar side of the brace as seen in FIGS. 1 & 2, positioned adjacent to the lateral aspect of the forearm and hand generally in line with the wrist joint.

At either end of the dampers is the mounting end or rod end 10 FIGS. 1 & 2. These ends have a compressed ball or spherical bearing mount which is free to swivel. This mounting end ball is placed between tapered compression blocks 12. Mounting screw 11 is inserted through mounting tab 17 or 17a, through a tapered compression block 12, through the rod end 10, then through another tapered compression block 12, and possibly through the other end of mounting tab 17 or 17a and finally is secured with a nut 13. This mounting allows approximately 40 degrees of free movement at each end. Dampers will typically be supplied from an outside source and are only defined in terms to understand their operation and relative function applications. Each damper (FIGS. 1 & 2) typically consists of a body 5, shaft 6, mounting ends 10, spring perches 8, spring 7, and internal valving and fluid which is not shown. The internal valving and fluid is changeable and provides adjustable degrees of damping from soft to firm. In essence, the rate or speed at which the shaft 6 compresses or releases from the body 5 is controlable and adjustable. The internal valving will cause shaft 6 to naturally resist higher input forces with higher resistance and lower input forces with lower resistance. This energy absorbing quality of the dampers will dampen or adsorb high and low energy inputs. In essence, the dampers will lessen the shock of a sudden impact helping to prevent injury and re-injury. The dampers will also absorb low energy inputs in turn helping to insulate the joint from vibrations that may be incurred while operating machinery or driving a car.

As shown in FIGS. 1 & 2 the spring perch 8 which is mounted on the shock body 5 is slideable on the shock body and is lockable at any position through tightening screw 9 on the spring perch 8. Therefore the spring compression may be easily varied to the desired force level. In addition, the spring 7 is easily changeable with other rate springs offering infinitely adjustable spring rates. These springs provide some of the force to the joint to promote movement or to provide resistance to movement.

Elastics such as in FIGS. 4, 5 & 6, caricature 28 are used to provide additional forces and resistance in extension, flexion, and ulnar/radial ranges. The elastics are easily hooked on the curved ends of the mounting tabs 17 & 17a, on the back of the slip link housing 3, and through mounting holes 19. By varying the weight, size and amount of elastics the force is infinitely adjustable. Elastics may also be used to neutralize the force of the springs and therefore provide one means to bias movement for any direction to compensate for weakened muscles or damaged nerves and ligaments. Other means to provide bias are to combine elastic use with slip link adjustment and spring tension adjustment.

Various length nylon clips 21 FIG. 2 are provided which are designed to be easily clipped onto the damper shaft 6. FIG. 2 shows the side damper with the spring removed for illustrative purposes. In the case of the dampers with springs mounted, the spring is simply pulled back/compressed and the clip 21 affixed. These clips will limit the range of compression of the damper or can completely lock the damper in the fully extended position. This is beneficial in the early days of post operative wrist rehabilitation when it is desirable to limit or lock out movement. With full length clips 21 installed on the top and side damper shafts 6 and the with the slip link locked, the brace is a rigid splint.

FIG. 4 illustrates a top view of the brace as worn by a user with an elastic installed to promote radial deflection. The elastic is slipped through mounting hole 19, back through itself, then stretched and hooked onto the top dampers's 34 front mounting tab 17. If desired, to help avoid compressive forces the top damper 34 may be locked fully extended with a clip 21 FIG. 2.

FIG. 5 shows the brace as worn by a user with an elastic 28 installed on the side damper mounting tabs 17 to promote ulnar deflection. If desired, to help avoid compressive forces the top damper may be locked fully extended with a clip 21. FIG. 2. This figure also shows the attachment of the D ring straps 35 FIGS. 5 & 7.

FIGS. 4, 5, & 6 show the brace promoting movement isolated to one deviation at a time. The interactive brace functions allow multiple inputs and offer unprecedented control to create the most desirable or applicable environment to help heal the wrist joint. Functions are interactive in the following senses: The brace can be set to hold the wrist in any combined position of flexion, extension, ulnar or radial deflection rigidly without allowing any movement and applying no forces. Or, while holding said position it can be set to apply an adjustable continuous force to promote movement in any of the deviations. It can be set to isolate force to one of the deviations or to apply force to a combination of deviations such as ulnar and extension at the same time. The brace can apply these interactive forces while allowing no movement or while allowing graduated ranges of movement. FIGS. 4, 5, & 6 show the positioning of the brace, more specifically the positions of the hand piece 2, the forearm piece 1 and the location of the variable stretch mounting strapping 35 which combined provide support to the transverse metacarpal ligaments, the carpal ligaments, the intercarpal ligaments and to the transcarpel ligaments.

FIG. 6 illustrates the brace as worn by the user with an elastic 28 installed from the rear of the slip link shroud 3 and hooked to the top dampers 34 front mounting tab 17. The top damper 34 should be locked fully extended with a clip 21 FIG. 2. This elastic and clip installation will promote upward movement of the hand around the wrist joint while avoiding the application of any compression forces to the wrist. This is illustrated by axis 29 which shows the pivot point that passes through the os capitatim bone. This application of upward rotational force without compression is ideal for treatment of wrist fractures requiring a dorsal transrelocation of the distal carpel row. This upward rotational force is achievable with any combination of pre-set ulnar/radial deflection or ulnar/radial range of motion/lock out. Ulnar/radial deflection may also be pre-loaded while allowing graduated ranges of movement in said position combined with the upward rotational force.

Figure 7:
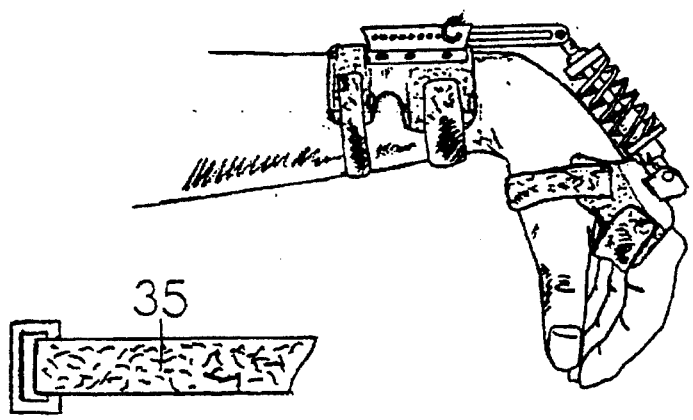
FIG. 7 shows the brace mounted on the wrist with the slip link locked in the fully extended position promoting extension in the wrist joint.

FIG. 7 shows the brace as worn by the user with the slip link 4 in the fully extended and locked position. It is possible to lock the link in many positions from fully retracted to fully extended. The locking pin 15 FIG. 3 is inserted through any hole 23 in the link housing 3 and through the end hole 24 in the slip link FIG. 3. This feature allows an adjustable application of downward rotational force to the hand and wrist joint. This can be used to apply an active volar transrelocation force to the distal carpel row. Extending the position of the slip link makes the top spring loaded damper increase downward force to the hand creating the volar transrelocation force while at the same time allowing movement of the radiocarpel joint through the resistive yet yielding action of the spring. Movement may also be avoided through inserting a full lock out clip 21 FIG. 2 on to the top damper shaft 6 which prevents the damper from compressing. The force is adjustable through varying spring rates, varying the length of the slip link and through adjusting the slideable, lockable spring perch 8 on the damper body 5. This application is interactive with any degree of pre-set ulnar/radial deflection, preload, or ranges of motion/lock out.

FIG. 7 also shows a segment view of the D ring loop strap. These straps may be supplied in varying degrees of stretch from zero stretch to approximately fifty percent stretch. The straps are one and one quarter to one and one half inches wide. The straps are slipped through slots 20 in the forearm piece and the hand piece, back through the D ring, then are fastened to the self adhesive hook strips 16 which are adhered to the forearm piece and hand piece.

FIG. 8 depicts a radial side view of the preferred embodiment. The D ring mounting straps are not shown.

The preferred embodiment of the present invention has been described in detail but it must be understood various changes and alterations may be made without departing from the scope and true spirit of the invention. FIGS. 9, 10, 11 & 12 show some alternate versions and components.

Figure 12:
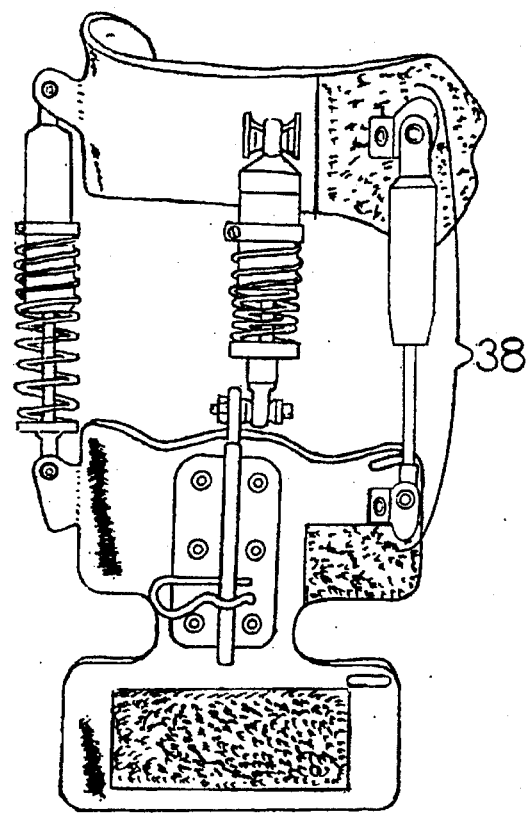
FIG. 12 illustrates a top view of another version of the brace showing the addition of a radially mounted third damper, the preferred slip link and hand piece.
Figure 13:
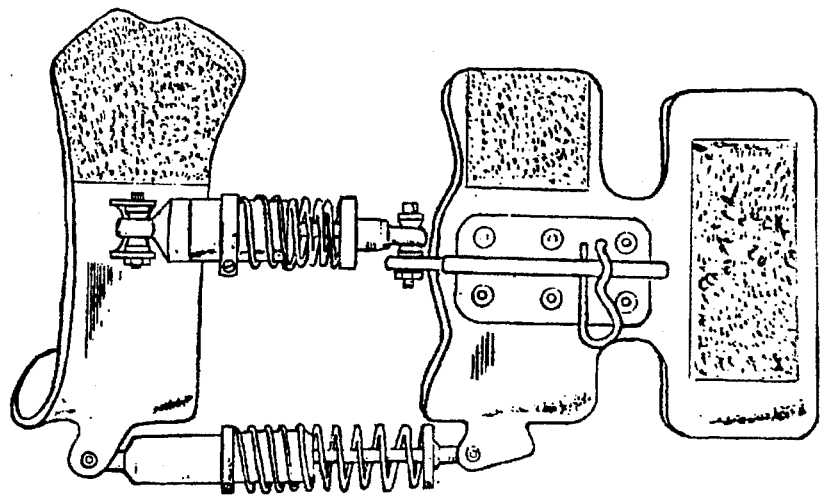
FIG. 13 illustrates the top view of the preferred embodiment.

FIG. 12 shows the preferred embodiment with an additional third radial side damper assembly 38 added. Although the spring is not shown on the third damper, adding the spring provides another way to bias ulnar/radial pre-load into the brace to compensate for weakened muscles or to provide equal extensive forces to the hand. In other words the brace can be set to apply force to pull the hand outward, away from the body or to push it inward toward the body.

Figure 10:
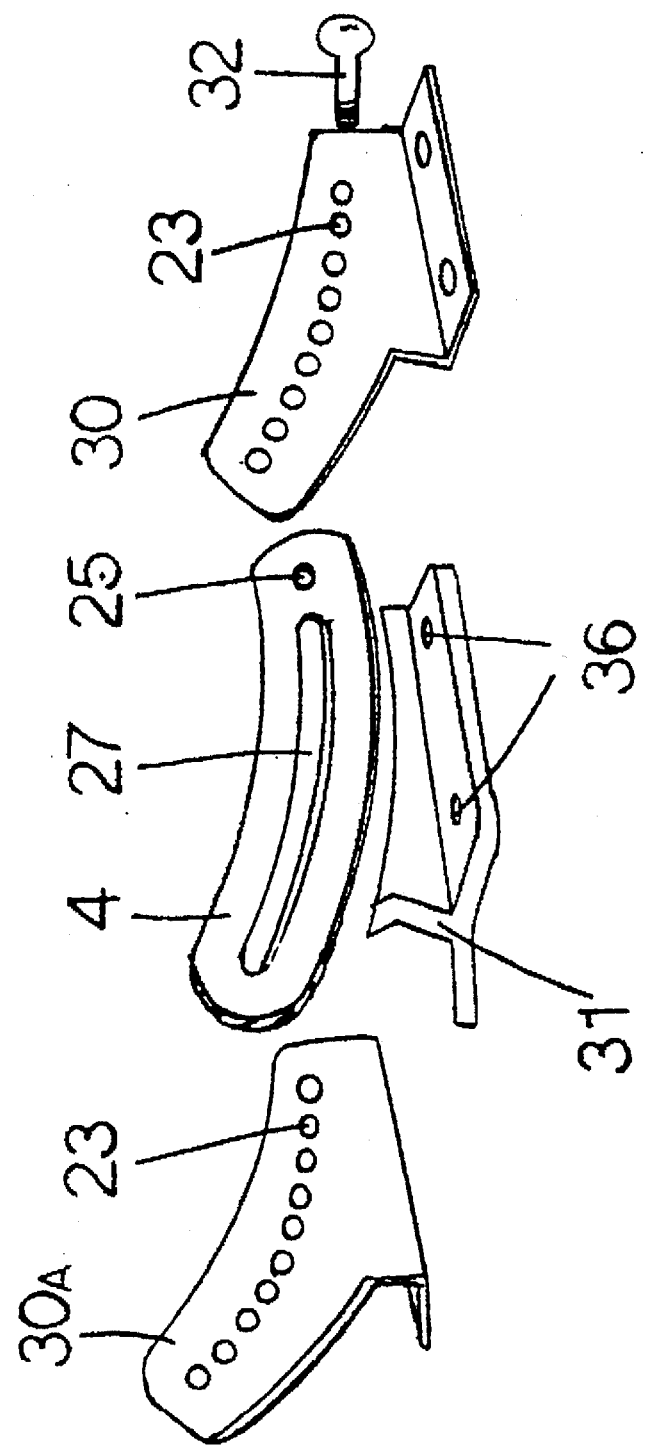
FIG. 10 is an enlarged and expanded view of a compression link.
Figure 11:
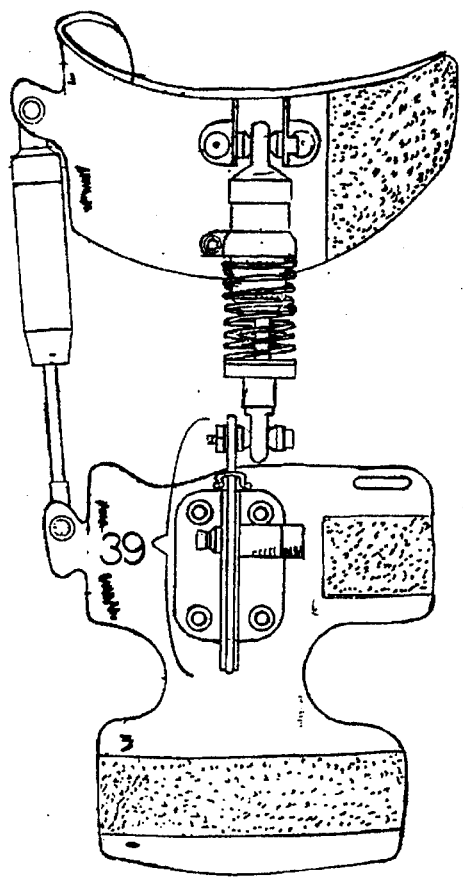
FIG. 11 is a top view of an alternative version of the brace showing a compression link on the top and no spring mounted on the ulnar damper. This version also illustrates an optional hand piece.

FIG. 11 shows a brace with a different style link other than the slip link such as a compression link assembly 39 FIG. 10 & 11 substituted for the slip link assembly. It also shows a smaller hand piece 2 and the ulnar damper without a spring.

FIG. 9 shows a radial side view of a brace fitted with a compression link 39 and less the D ring mounting straps. Of particular importance to this type link is 33 the compression link guide. This guide holds the link 4 in place.

FIG. 10 illustrates an enlarged expanded view of a compression link. The slip link 4 FIG. 3 has a modified curved configuration yet retains the center slot 27 and the front damper mounting hole 25. This link rides on a nylon saddle 31 which is sandwiched between and under the side pieces 30. One side 30a of the link is threaded to accept the thumb screw 32. Two thumb screws 32 may be used and placed in any holes to limit link travel. Tightening the screws will compress the sides 30 and lock the link 4 in the desired position.

Even though several alternative versions are shown, it is the intent of the invention to encompass any version utilizing spring loaded dampers whether passive or active with either fixed or adjustable slideable mounting, that are used in controlling the hand or wrist joint.

I claim:

1. A wrist brace, comprising:

first means for releasably enveloping a hand;

second means for releasably enveloping a wrist;

means for articulatingly coupling said first and second means together in a spaced apart relationship; wherein said first and second means have a top surface and a side surface and;

said coupling means comprises means for intercoupling said top surfaces, and intercoupling said side surfaces; wherein said intercoupling means comprise means for damping any movement of said first and second means toward or away from each other.

2. A wrist brace, according to claim 1, wherein:

said damping means comprises a body, and a shaft reciprocable relative to, and within, said body;

an end of said shaft is pivotably coupled to one of said first and second means; and an end of said body is pivotably coupled to the other of said first and second means.

3. A wrist brace, according to claim 2 wherein:

said damping means further comprises means for biasingly urging said shaft and body together and apart.

4. A wrist brace, according to claim 3, wherein:

said urging means comprises a compression spring.

5. A wrist brace, according to claim 2, further including:

means slidably engageable with said shaft for selectively limiting reciprocation of said shaft within said body.

6. A wrist brace, according to claim 1, wherein:

said damping means comprises a body, a shaft reciprocable within said body;
said body contains a viscous fluid;
an end of said shaft is coupled to a link;
an end of said body is coupled to said first means; and
said link is movably coupled to said second means.

7. A wrist brace, according to claim 6, further including:
a link housing coupled to said second means; and
said link is slidably engaged with said housing.

8. A wrist brace, according to claim 7, wherein:
said housing comprises a channel; and
said link is reciprocable within said channel.

9. A wrist brace, according to claim 8, wherein:
said housing and said link have means mutually cooperative for (a) prohibiting movement of said link within said channel, and (b) selectively limiting movement of said link within said channel.

10. A wrist brace, according to claim 8, wherein:
said housing has a plurality of holes formed therein; and
said link has a hole formed therein alignable with any of said holes of said plurality thereof in said housing.

11. A wrist brace, according to claim 8, wherein:
said housing has a plurality of holes formed therein; and
said link has a longitudinal slot formed therein.

* * * * *